United States Patent [19]

Obrecht

[11] Patent Number: 4,741,767

[45] Date of Patent: May 3, 1988

[54] 2H-IMIDAZO(1',2':1,2)PYRROLO(3,4-B)PYRIDINE COMPOUNDS, AND THEIR USE AS HERBICIDAL AGENTS

[75] Inventor: Jean-Pierre Obrecht, Schlieren, Switzerland

[73] Assignee: Hoffmann-La Roche Inc., Nutley, N.J.

[21] Appl. No.: 795,570

[22] Filed: Nov. 6, 1985

[30] Foreign Application Priority Data

Nov. 16, 1984 [CH] Switzerland .......................... 5490/84
Aug. 27, 1985 [CH] Switzerland .......................... 3675/85

[51] Int. Cl.$^4$ ..................... A01N 43/40; A01N 57/08; C07D 471/14; C07F 9/06
[52] U.S. Cl. ............................................. 71/94; 71/86; 546/15; 546/23; 546/82
[58] Field of Search ................ 546/15, 82, 23; 71/86, 71/94

[56] References Cited

FOREIGN PATENT DOCUMENTS

| 0041623 | 12/1981 | European Pat. Off. ............... 546/82 |
| 133309 | 2/1985 | European Pat. Off. ............... 546/82 |
| 2700269 | 7/1978 | Fed. Rep. of Germany ........ 546/82 |
| 2700270 | 7/1978 | Fed. Rep. of Germany ........ 546/82 |

*Primary Examiner*—Richard A. Schwartz
*Assistant Examiner*—J. Richter
*Attorney, Agent, or Firm*—Jon S. Saxe; George M. Gould; Julie M. Prlina

[57] ABSTRACT

The invention is concerned with novel weed control compositions which contain herbicidally-active compounds of the formula

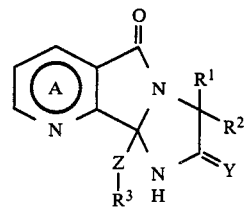

wherein ring A, $R^1$, $R^2$, $R^3$, Y and Z are as hereinafter set forth, and the use of these compounds and compositions for the control of weeds. The invention is also concerned with novel compounds of formula I as well as their preparation.

14 Claims, No Drawings

2H-IMIDAZO(1',2':1,2)PYRROLO(3,4-B)PYRIDINE COMPOUNDS, AND THEIR USE AS HERBICIDAL AGENTS

DETAILED DESCRIPTION OF THE INVENTION

The present invention is concerned with weed control compositions which contain herbicidally-active heterocyclic compounds. These compounds are 2H-imidazo[1',2':1,2]pyrrolo[3,4-b]pyridines of the general formula

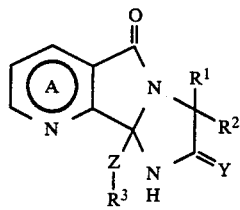   I wherein the pyridine ring A can be optionally substituted, and $R^1$ is $C_{1-4}$-alkyl optionally mono- or multiply-substituted with fluorine and/or chlorine, $R^2$ is $C_{1-10}$-alkyl or $C_{3-6}$-cycloalkyl, or $R^1$ and $R^2$ together with the carbon atom to which they are attached are a $C_{3-6}$-cycloalkane ring optionally substituted with one or two $C_{1-4}$-alkyl residues.

$R^3$ is hydrogen; unsubstituted branched alkyl with up to 12 carbon atoms; straight-chain or branched $C_{1-12}$-alkyl substituted with one or more halogen atoms, one or more hydroxyl groups, a cyano group, a $C_{3-6}$-cycloalkyl group, a $C_{1-4}$-alkoxy group, a pyridyl group, an optionally substituted phenoxy group, an α- or β-naphthyloxy group or one of the groups (c)–(j)

—CO—R⁶   (c)

wherein
$R^6$ is hydrogen, hydroxy, $C_{1-4}$-alkyl, $C_{1-4}$-alkoxy or phenyl;

—SO$_n$,R⁷   (d)

wherein
$R^7$ is hydroxy, methyl, phenyl, or p-tolyl and n' is 0, 1 or 2; with the proviso that n' is 2 when $R^7$ is hydroxy, —OSO₂R⁷   (e)

wherein $R^7$ is as described above;

an optionally esterified phosphite, phosphate or phosphonate group;   (f)

especially one of the formula

—(O)$_{n''}$P(O)$_{n''}$(R⁸)₂   (f')

wherein the two symbols
$R^8$ each independently are hydroxy, $C_{1-4}$-alkoxy or phenoxy and
the two symbols n" each independently are 0 or 1, with the proviso that their sum is 1 or 2;

—NHCONHR⁹   (g)

wherein $R^9$ is hydrogen, $C_{1-4}$-alkyl or phenyl,

—NHCOOR¹⁰   (h)

wherein $R^{10}$ is $C_{1-4}$-alkyl;

—OCONHR⁹   (i)

wherein $R^9$ is as defined above;

—OCO(CH₂)$_n$·COR¹¹   (j)

wherein
$R^{11}$ is hydroxy, $C_{1-4}$-alkoxy, phenoxy or benzyloxy and
n' is as defined above; $C_{3-10}$-alkynyl; $C_{3-6}$-cycloalkyl; or a group (a) or (b)

   (a)

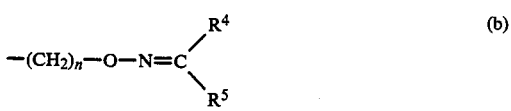   (b)

$R^4$ and $R^5$ each independently are $C_{1-4}$-alkyl,
n is 1 or 2, and
Y and Z each independently are oxygen or sulfur, with the exception of 1,9b-dihydro-9b-hydroxy-3-isopropyl-3-methyl-2-thioxo-2H-imidazo[1,',2':1,2-]pyrrolo[3,4-b]pyridin-5(3H)-one, i.e. the compound of the formula

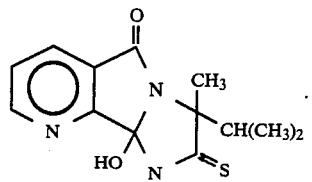

The pyridine ring A which is present in formula I can optionally carry up to 3 substituents. There come into consideration as substituents especially halogen, $C_{1-6}$-alkyl, trifluoromethyl, $C_{1-4}$-hydroxyalkyl, $C_{1-6}$-alkoxy, $C_{1-6}$-alkylthio, nitro, cyano, methylsulphonyl, phenylsulphonyl, p-tolylsulphonyl and optionally substituted phenyl, phenoxy, phenylthio and benzyloxy. The substituents can be the same or different. Further, the pyridine ring A can also have a fused benzene, pyridine or pyrazine ring as a substituent, in accordance with one of the following partial structures:

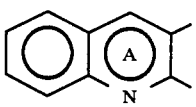

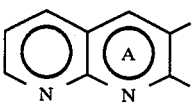

-continued

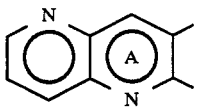

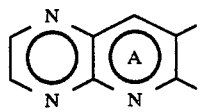

in which ring A can also carry a substituent in the 4-position, especially one of the substituents indicated above in connection with the pyridine ring A.

In the above descriptions concerning the substituents on the pyridine ring A the term "halogen" embraces fluorine, chlorine, bromine and iodide. The alkyl residue can be straight-chain or branched and this also applies to the alkyl part of the hydroxyalkyl, alkoxy or alkylthio group. As substituents on the substituted phenyl, phenoxy, phenylthio or benzyloxy group there come into consideration especially 1 to 3 substituents which are preferably selected from 1 to 3 halogen atoms, 1 or 2 $C_{1-4}$-alkyl residues, a trifluoromethyl group, 1 or 2 $C_{1-4}$-alkoxy groups, 1 or 2 nitro groups and a cyano group, whereby also in this case "halogen" embraces fluorine, chlorine, bromine and iodine and the "alkyl residues" and "alkoxy groups" embrace straight-chain and branched groups.

The alkyl or haloalkyl group represented by $R^1$ or the alkyl group represented by $R^2$, $R^4$ or $R^5$ can be straight-chain or branched and this also applies to the alkyl substituents of the $C_{3-6}$-cycloalkane ring which can be formed by $R^1$ and $R^2$ together with the carbon atom carrying these and which is substituted with one or two $C_{1-4}$-alkyl residues.

In the above and following descriptions concerning the substituents on the alkyl residue $R^3$ there is always to be understood under "halogen" fluorine, chlorine, bromine or iodine. Any alkyl or alkoxy group present can be straight-chain or branched.

When $R^3$ is haloalkyl or hydroxyalkyl, this group preferably has 1–5 halogen atoms or 1–11, especially 1–6, hydroxy groups. The halogen atoms are preferably fluorine and/or chlorine atoms. Examples of such groups are 2,2,2-trifluoroethyl, 2-chloroethyl and 2,2,3,3,3-pentafluoropropyl or 2-hydroxyethyl and 2,3-dihydroxypropyl. When $R^3$ is cycloalkylalkyl, then this preferably contains a total of 4–12 carbon atoms. As substituents on the substituted phenoxy group there come into consideration especially 1–3 substituents which are preferably selected from 1–3 halogen atoms, 1 or 2 $C_{1-4}$-alkyl groups, a trifluoromethyl group, 1 or 2 $C_{1-4}$-alkoxy groups, 1 or 2 nitro groups and a cyano group, whereby any alkyl or alkoxy group present is preferably methyl or methoxy, respectively. The pyridyl group can be 2-, 3- or 4-pyridyl, but it is preferably 3-pyridyl.

The above-defined carboxyl group (group (c) in which $R^6$ is hydroxy); sulphonic acid group (group (d) in which $R^7$ is hydroxy); sulphate group (group (e) in which $R^7$ is hydroxy); optionally esterified phosphite, phosphate or phosphonate group (f) in which at least one hydroxyl group is present, especially a group (f') in which at least at one of the symbols $R^8$ stands for hydroxy; or carboxy(alkyl)-carbonyloxy group (group (j)) in which $R^{11}$ is hydroxy) is always intended to include their metal or optionally substituted ammonium salts, especially the alkali metal such as sodium or potassium, alkaline earth metal such as calcium or magnesium, manganese, copper, iron, zinc, cobalt, lead, silver, nickel, ammonium or mono- or multiply alkylated ammonium salts.

In group (c) $R^6$ is preferably methyl or ethoxy and in group (d) $R^7$ is preferably methyl and independently thereof n' is preferably 0 or 2. Where group (c), (d), (e), (f), (f') or (j) is present in the form of a mono- or multiply alkylated ammonium salt, then the alkyl substituents are especially $C_{1-4}$-alkyl residues. The substituted ammonium ion is preferably triethylammonium. In the group (f') the two symbols $R^8$ each individually preferably signify hydrogen, methyl or ethyl, whereby it is especially preferred that the two symbols $R^8$ have the same significance. Especially preferred groups (f') are the phosphate group and the dimethyl and diethyl esters thereof. Finally, $R^9$, $R^{10}$, $R^9$ or $R^{11}$ in group (g), (h), (i) or (j) preferably signifies methyl; methyl; hydrogen, methyl or phenyl; or hydroxy or a salt thereof, especially the triethylammonium salt, respectively.

The alkynyl group represented by $R^3$ can be straight-chain or branched and can have one or more triple bonds.

If the pyridine ring A is substituted, then the substituents are preferably 1–3 halogen atoms, especially fluorine, chlorine and/or bromine, particularly one chlorine atom; 1 or 2 alkyl residues, especially one alkyl residue, particularly methyl or ethyl; a trifluoromethyl group; a hydroxyalkyl group, especially hydroxymethyl; 1 or 2 alkoxy groups, especially one alkoxy group, particularly ethoxy; an alkylthio group, especially methylthio; 1 or 2 nitro groups, especially one nitro group; a cyano group; and/or an optionally substituted phenyl, phenoxy, phenylthio or benzyloxy group. Not more than two substituents are preferably present and a single substituent, particularly halogen, $C_{1-6}$-alkyl or $C_{1-6}$-alkoxy, is particularly preferred. If the pyridine ring A features a fused benzene, pyridine or pyrazine ring, then this is preferably a benzene ring. The pyridine ring is, however, preferably unsubstituted.

Independently of one another $R^1$ preferably is unsubstituted $C_{1-4}$-alkyl, especially methyl; $R^2$ preferably is $C_{1-10}$-alkyl, especially isopropyl; and $R^3$ preferably is hydrogen, optionally substituted alkyl as defined above, $C_{3-10}$-alkynyl or $C_{3-6}$-cycloalkyl. Of the substituted alkyl groups $R^3$ there are preferred hydroxyalkyl, cyanoalkyl, cycloalkylalkyl, alkoxyalkyl, optionally substituted phenoxyalkyl and alkyl substituted with a group (d) or (h), with hydroxyalkyl, cycloalkylalkyl, alkoxyalkyl and optionally substituted phenoxyalkyl being especially preferred. However, unsubstituted branched alkyl, especially isopropyl and isobutyl, as well as alkoxyalkyl, especially 2-methoxy- and 2-ethoxy-ethyl, are of primary interest.

The presence of at least one asymmetric carbon atom in the compounds of formula I means that the compounds can occur in the form of optical isomers. When an aliphatic C=C double bond is present geometric isomerization can also occur. Formula I is intended to embrace all of these possible isomeric forms.

Especially preferred compounds of formula I are:
1,9b-Dihydro-9b-isopropoxy-3-isopropyl-3-methyl-2H-imidazo[1',2':1,2]pyrrolo[3,4-b]pyridine-2,5(3H)-dione, 1,9b-dihydro-9b-isobutoxy-3-isopropyl-3-methyl-2H-imidazo[1',2':1,2]pyrrolo[3,4-b]pyridine-2,5(3H)-dione, 1,9b-dihydro-3-isopropyl-9b-(2-methoxyethoxy)-3-methyl-2H-imidazo[1',2':1,2]pyrrolo[3,4-b]pyridine-2,5(3H)-dione and 9b-(2-ethoxyethoxy)-1,9b-dihydro-3-isopropyl-3-methyl-2H-imidazo[1',2':1,2]pyrrolo[3,4-b]pyridine-2,5(3H)-dione.

Further representative compounds of formula I are:

1,9b-dihydro-9b-isopropoxy-3-isopropyl-3-methyl-2-thioxo-2H-imidazo[1',2':1,2]pyrrolo[3,4-b]pyridin-5(3H)-one, 1,9b-dihydro-3-isopropyl-3-methyl-9b-[2-(3-methylureido)-ethoxy]-2H-imidazo[1',2':1,2]pyrrolo[3,4-b]pyridine-2,5(3H)-dione, 1,9b-dihydro-3-isopropyl-9b-[2-(isopropylideneamino)oxyethoxy]-3-methyl-2H-imidazo[1',2':1,2]pyrrolo[3,4-b]pyridine-2,5(3H)-dione, 1,9b-dihydro-3-isopropyl-9b-[(isopropylideneamino)oxy]-3-methyl-2H-imidazo[1',2':1,2]pyrrolo[3,4-b]pyridine-2,5(3H)-dione, 1,9b-dihydro-3-isopropyl-3-methyl-9b-{2-[(methylcarbamoyl)oxy]-ethoxy}-2H-imidazo[1',2':1,2]pyrrolo[3,4-b]pyridine-2,5(3H)-dione, 1,9b-dihydro-3-isopropyl-3-methyl-9b-[2-(sulphooxy)ethoxy]-2H-imidazo[1',2':1,2]pyrrolo[3,4-b]pyridine-2,5(3H)-dione sodium salt.

1,9b-dihydro-3-isopropyl-3-methyl-9b-[2-(phosphonooxy)ethoxy]-2H-imidazo[1',2':1,2]pyrrolo[3,4-b]pyridine-2,5(3H)-dione, 1,9b-dihydro-3-isopropyl-3-methyl-9b-(3,3,3-trifluoropropoxy)-2H-imidazo[1',2':1,2]pyrrolo[3,4-b]pyridine-2,5(3H)-dione, 1,9b-dihydro-9b-(2,3-dihydroxypropoxy)-3-isopropyl-3-methyl-2H-imidazo[1',2':1,2]pyrrolo[3,4-b]pyridine-2,5-(3H)-dione, 9b-{2-[[2-[(benzyloxy)carbonyl]ethyl]carbonyloxy]-ethoxy}-1,9b-dihydro-3-isopropyl-3-methyl-2H-imidazo[1',2':1,2]pyrrolo[3,4-b]pyridine-2,5(3H)-dione, 9b-{2-[[(2-carboxyethyl)carbonyl]oxy]-ethoxy}-1,9b-dihydro-3-isopropyl-3-methyl-2H-imidazo[1',2':1,2]pyrrolo[3,4-pyridine-2,5(3H)-dione, 9b-{2-[[(carboxyethyl)carbonyl]oxy]-ethoxy}1,9b-dihydro-3-isopropyl-3-methyl-2H-imidazo[1',2':1,2]pyrrolo[3,4-b]pyridine-2,5(3H)-dione sodium salt and 1,11b-dihydro-11b-isopropoxy-3-isopropyl-3-methyl-2H-imidazo[1',2':1,2]pyrrolo[3,4-b]quinoline-2,5(3H)-dione, With the exception of 1,9b-dihydro-9b-hydroxy-3-isopropyl-3-methyl-2-thioxo-2H-imidazo[1',2':1,2]pyrrolo[3,4-b]pyridin-5(3H)-one (see above) as well as 1,11b-dihydro-11b-hydroxy-3-isopropyl-3-methyl-2H-imidazo[1',2':1,2]pyrrolo[3,4-b]quinoline-2,5(3H)-dione, i.e. the compound of the formula

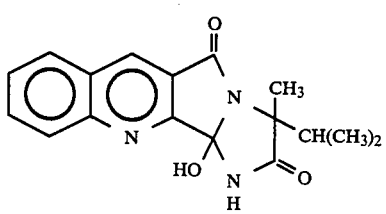

the compounds of formula I are novel compounds. These novel compounds of formula I as well as the process for the preparation of these compounds also form objects of the present invention.

The known compounds and their manufacture are described on pages 57-59 of European Patent Publication No. 133,309 and on page 165 of European Patent Publication No. 41,623, respectively. Nothing is indicated in E.P. No. 41,623 concerning the possible use of the second-named compound.

The process in accordance with the invention for the manufacture of the novel compounds of formula I comprises reacting a compound of the formula

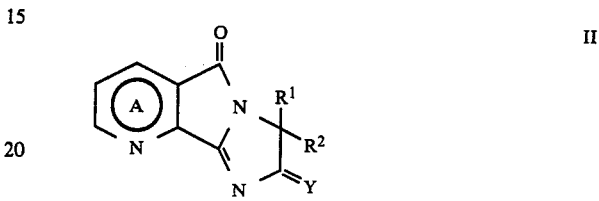

wherein ring A, $R^1$, $R^2$ and Y are as defined above, with a compound of the formula

wherein $R^3$ and Z are as defined above.

The reaction is conveniently carried out in a diluent at temperatures between −20° C. and 100° C., but preferably between 0° C. and 40° C. Moreover, the reaction is advantageously carried out in the presence of an acidic catalyst. As diluents there are especially suitable organic solvents, preferably aprotic organic solvents such as halogenated hydrocarbons, e.g. methylene chloride and chloroform, and aliphatic or cyclic ethers, e.g. diethyl ether and tetrahydrofuran. Preferred acidic catalysts are organic acids such as acetic acid, trifluoroacetic acid and p-toluenesulphonic acid; inorganic acids such as hydrogen chloride, Lewis acids such as titanium tetrachloride and aluminium chloride; polymer-bound acids; polymeric acids; and silica gel.

The isolation and the purification of the thus-manufactured compounds of formula I can be carried out in a manner known per se.

The starting materials of formula II in which Y signifies oxygen are either known or can be produced according to methods known per se, e.g. in accordance with European Patent Publication No. 41,623 (see especially pages 9, 10, 29-33, 35-40, 43, 44, 49, 50, 52-59, 61-64, 74-80, 101-104, 114, 137, 138 and 140-147). The method described therein leads mainly to the imidazopyrrolopyridinedione of formula II, but there simultaneously results as a byproduct in a small amount the corresponding geometric isomer of the general formula

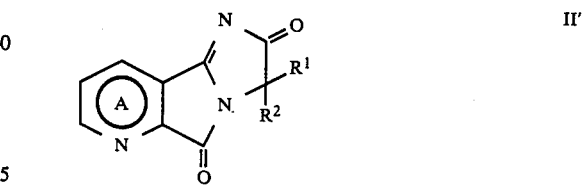

wherein ring A, $R^1$ and $R^2$ are as defined above, see in this respect page 30, line 26 to page 31, line 24, page 33 and page 78 (Example 3) of EP No. 41,623. This by-product can be removed in a manner known per se at this stage or can be reacted together with the compound of formula II in which Y is oxygen with the compound of formula III to manufacture the product of formula I. In the latter case, in addition to the compound of formula I, there results in a small amount the compound of the formula

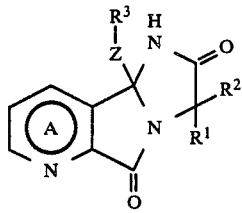 I' wherein ring A, $R^1$, $R^2$, $R^3$ and Z are as defined above.

Where desired, the desired product of formula I can subsequently be freed in a manner known per se from the byproduct of formula I'.

The starting materials of formula II in which Y is sulfur can, for their part, be produced by treating a nitrile of the general formula

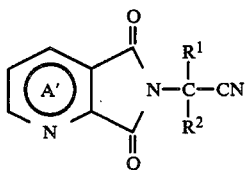 IV wherein ring A, $R^1$ and $R^2$ are as defined above, with gaseous hydrogen sulfide and subjecting the thioamide of the general formula

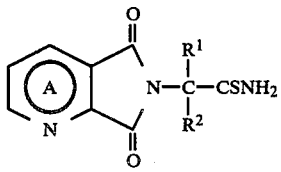 V which results therefrom to a base- or acid-catalyzed cyclization.

The treatment with gaseous hydrogen sulfide is conveniently carried out in an inert diluent at temperatures between 0° and 100° C., preferably between 0° and 20° C., until saturation. Suitable diluents are organic aprotic solvents such as halogenated hydrocarbons, e.g. methylene chloride and chloroform, and secondary or tertiary lower alkanols, e.g. isopropanol and tert.butanol. After saturating the reaction mixture with hydrogen sulphide it is advantageously left to stand for 1 to 7 days, whereafter the isolation and the purification of the thioamide of formula V can be carried out in a manner known per se.

The cyclization of the thioamide to the starting material of formula II can be carried out in a manner known per se, e.g. an analogously to the cyclization of 5,7-dihydro-α-isopropyl-α-methyl-5,7-dioxo-6H-pyrrolo[3,4-b]pyridine-6-acetamide which is described in Example 3 (page 78) of European Patent Publication No. 41,623. In the cyclization of the thioamide of formula V there is also usually produced as a byproduct in a small amount the corresponding geometric isomer of the formula

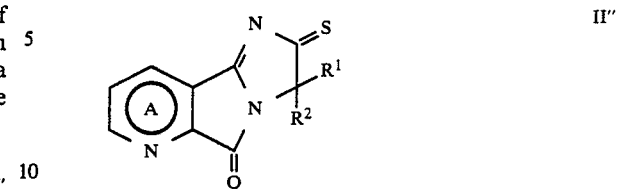 II'' wherein ring A, $R^1$ and $R^2$ are as defined above. The above remarks also apply to this byproduct: the corresponding byproduct of I is accordingly the compound of the formula

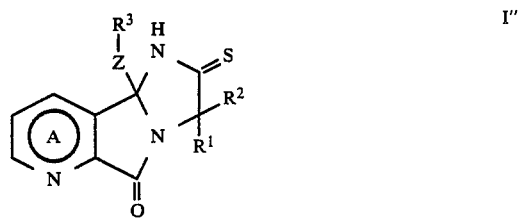 I'' wherein ring A, $R^1$, $R^2$, $R^3$ and Z are as defined above.

The nitriles of formula IV within which are used in this two-stage process are either known or can be produced according to methods known per se (see e.g. European Patent Publication No. 41,623).

A further method for the production of the starting materials of formula II comprises subjecting a nicotinic acid of the general formula

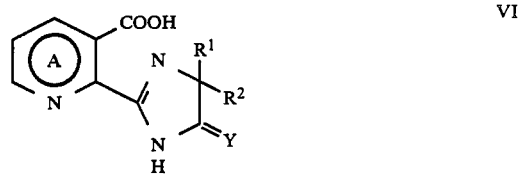 VI wherein ring A, $R^1$, $R^2$ and Y are as defined above, to a cyclization and water-cleavage. When Y in formula VI signifies oxygen, the cyclization is conveniently carried out by heating the nicotinic acid VI in a mixture of acetic anhydride and acetic acid, which simultaneously serves as the solvent, at reflux temperature. After removing the solvent, e.g. by evaporation under reduced pressure, the product can be purified according to methods known per se. On the other hand, if Y in formula VI represents sulphur, there are conveniently used trifluoroacetic anhydride as the water-elimination agent as well as an organic solvent such as an aliphatic chlorinated hydrocarbon, e.g. methylene chloride or chloroform; in this case the reaction is carried out at low temperatures, especially in the temperature range −80° C. to −40° C.

The nicotinic acids of formula VI are either known or can be produced according to methods known per se (see e.g. European Patent Publication No. 133,309).

The starting materials of formula III are either known or can be produced according to methods known per se.

The compounds of formula I possess herbicidal properties and are especially suitable for the control of weeds, especially of barnyard grass (*Echinochloa crusgalli*), greater foxtail millet (*Setaria faberii*), resistant brome (*Bromus inernis*), quackgrass (*Agropyron repens*), hairy crab grass (*Digitaria sanguinalis*), white goosefoot (*Chenopodium album*), redroot amaranth (*Amaranthus retroflexus*), charlock (*Sinapsis arvensis*), common thorn apple (*Datura stramonium*), catchweed (*Galium aparine*) and common cocklebur (*Xanthium pensylvanicum*) in diverse food plant cultivations. Certain representative compounds of formula I are suitable as selective herbicides in cultivated plants, especially in soya (*Gycine max*), maize (*Zea mays*) and wheat (*Tritia aestivum*) cultivations, others are suitable as total herbicides for the control of weeds in cereal or maize crops or as herbicides for use on industrial areas, roadsides and paths.

In general, a concentration of 100–1000 g of active substance of formula I/ha, preferably 200–500 g of active substance of formula I/ha, is sufficient to produce the desired herbicidal effect.

The compounds of formula I are not only pre-emergence herbicides but also post-emergence herbicides, whereby as the latter the compounds are especially effective on the leaves.

The weed control composition in accordance with the invention contains an effective amount of at least one compound of formula I, as defined above, as well as formulation adjuvants. The composition conveniently contains at least one of the following formulation adjuvants: solid carrier substances; solvents or dispersion media; tensides (wetting and emulsifying agents); dispersing agents (without tenside action); and stabilizers. With the use of these and other adjuvants the compounds of formula I, namely the herbicidally active substances, can be converted into the usual formulations such as dusts, powders, granulates, solutions, emulsions, suspensions, emulsifiable concentrates, pastes and the like.

The compounds of formula I are generally insoluble in water and can be formulated according to methods which are usual for water-insoluble compounds using the respective formulation adjuvants. The manufacture of the compositions can be carried out in a manner known per se, e.g. by mixing the respective active substance with solid carrier substances, by dissolution or suspension in suitable solvents or dispersion media, if necessary using tensides as wetting or emulsifying agents and/or dispersing agents, by diluting pre-prepared emulsifiable concentrates with solvents or dispersion media etc.

As solid carrier substances there essentially come into consideration: natural mineral substances such as chalk, dolomite, limestone, aluminas and silicic acid and salts thereof (for example, siliceous earth, kaolin, bentonite, talc, attapulgite and montmorillonite); synthetic mineral substances such as highly dispersible silicic acid, aluminium oxide and silicates; organic substances such as cellulose, starch, urea and synthetic resins; and fertilizers such as phosphates and nitrates, whereby such carrier substances can be present e.g. as powders or as granulates.

As solvents or dispersion media there essentially come into consideration: aromatics such as benzene, toluene, xylenes and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol, as well as their ethers and esters; ketones such as acetone, methyl ethyl ketone, methyl isobutyl ketone and cyclohexanone; and strongly polar solvents or dispersion media such as dimethylformamide, N-methylpyrrolidone and dimethyl sulphoxide, such solvents preferably having flash points of at least 30° C. and boiling points of at least 50° C., and water. Among the solvents or dispersion media there also come into consideration so-called liquified gaseous extenders or carrier substances, these being products which are gaseous at room temperature and under normal pressure. Examples of such products are especially aerosol propellants such as halogenated hydrocarbons, e.g. dichlorodifluoromethane. If the weed control composition in accordance with the invention is present in the form of a pressurized pack, then a solvent is conveniently used in addition to the propellant.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulphate, octadecyl sodium sulphate and cetyl sodium sulphate; alkyl sulphonates, aryl sulphonates and fattyaromatic sulphonates such as alkylbenzene sulphonates, e.g. calcium dodecylbenzene sulphonate, and butylnaphthalene sulphonates; and more complex fatty sulphonates, e.g. the amide condensation products of oleic acid and N-methyltaurine and the sodium sulphonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there essentially come into consideration: lignin, sodium and ammonium salts of lignin sulphonic acids, sodium salts of maleic anhydride-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents, e.g. epichlorohydrin, phenyl glycidyl ether and soya epoxides; antioxidants, e.g. gallic acid esters and butylhydroxytoluene, UV-absorbers, e.g. substituted benzophenones, diphenylacrylonitrile acid esters and cinnamic acid esters; and deactivators, e.g. salts of ethylenediaminotetraacetic acid and polyglycols.

The weed control compositions in accordance with the invention can contain, in addition to the compounds of formula I, synergists and other active substances, e.g. insecticides, acaricides, fungicides, plant growth regulators and fertilizers. Such combination compositions are suitable for intensifying the activity or for broadening the spectrum of activity.

The weed control compositions in accordance with the invention generally contain between 0.01 and 95 weight percent, preferably between 0.5 and 75 weight percent, of one or more compounds of formula I as the active substance(s). They can be present e.g. in a form which is suitable for storage and transport. In such formulations, e.g. emulsifiable concentrates, the active substance concentration is normally in the higher range, preferably between 1 and 50 weight percent, especially between 10 and 20 weight percent. These formulations can then be diluted, e.g. with the same or different inert substances, to give active substance concentrations which are suitable for practical use, i.e. preferably about 0.01 to 10 weight percent, especially about 0.5 to 5 weight percent. The active substance concentrations can, however, also be smaller or greater.

As mentioned above, the preparation of the weed control compositions in accordance with the invention can be carried out employing conventional techniques.

For the preparation of pulverous preparations the active substance, i.e. at least one compound of formula I, can be mixed with a solid carrier substance, e.g. by grinding together; or the solid carrier substance can be impregnated with a solution or suspension of the active substance and then the solvent or dispersion medium can be removed by evaporation, heating or filtering-off under reduced pressure. By adding tensides or dispersing agents such pulverous preparations can be made readily wettable with water, so that they can be converted into aqueous suspensions which are suitable e.g. as spray compositions.

The compound of formula I can also be mixed with a tenside and a solid carrier substance to form a wettable powder which is dispersible in water, or it can be mixed with a solid pre-granulated carrier substance to form a product in the form of a granulate.

When desired, the compound of formula I can be dissolved in a water-immiscible solvent such as, for example, a high-boiling hydrocarbon, which conveniently contains dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The use of the weed control compositions in accordance with the invention can be carried out according to usual application methods such as sprinkling, spraying, dusting, watering or scattering. The method in accordance with the invention for the control of weeds comprises treating the locus to be protected against weeds and/or the weeds with a compound of formula I in accordance with the invention or a weed control composition in accordance with the invention.

The following Examples serve to illustrate the invention in more detail.

I. PREPARATION OF THE ACTIVE SUBSTANCES OF FORMULA I

Example 1

100 g of silica gel are added to a solution of 200 g of 3-isopropyl-3-methyl-2H-imidazo[1',2':1,2]pyrrolo[3,4-b]pyridine-2,5(3H)-dione in 900 ml of isopropyl acetate and 100 ml of absolute isopropanol, and the resulting suspension is then stirred at room temperature for about 16 hours. The mixture is subsequently filtered, the filtrate is evaporated to dryness and the residue is crystallized from ethyl acetate/n-hexane. There is obtained 1,9b-dihydro-9b-isopropoxy-3-isopropyl-3-methyl-2H-imidazo[1',2':1,2]pyrrolo[3,4-b]pyridine-2,5(3H)-dione as colorless crystals, m.p. 158°–160° C.

Example 2

A solution of 2 g of 3-isopropyl-3-methyl-2H-imidazo[1',2':1,2]pyrrolo[3,4-b]pyridine-2,5(3H)-dione in 90 ml of methylene chloride and 10 ml of 2-ethoxyethanol is treated with 0.5 ml of trifluoroacetic acid and the reaction mixture is stirred at room temperature for 60 minutes. The mixture is subsequently evaporated to dryness under reduced pressure and the residue is crystallized from ethyl acetate/n-hexane. There are thus obtained colorless crystals, m.p. 115°–117° C., of 9b-(2-ethoxyethoxy)-1,9b-dihydro-3-isopropyl-3-methyl-2H-imidazo[1',2':1,2]pyrrolo[3,4-b]pyridine-2,5(3H)-dione.

Examples 3–36

The appropriate starting materials of formulae II and III are reacted analogously to the procedures described in Example 1 or 2 in order to manufacture the compounds of formula Ia or Ib listed in the following Tables 1 and 2.

TABLE 1

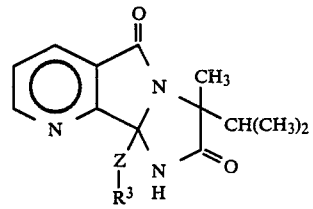

Ia

| Example | R³ | Z | M.p. (°C.) |
|---|---|---|---|
| 3 | —CH(CH₃)₂ | S | 132–134 |
| 4 | —CH₂CH(CH₃)(C₂H₅) | O | 131–133 |
| 5 | —CH(CH₃)(C₂H₅) | S | 126–128 |
| 6 | —CH₂—C≡CH | O | 135–137 |
| 7 | Cyclohexyl | O | 147–148 |
| 8 | —CH₂CH₂OH | O | 130–132 |
| 9 | —CH₂CH₂NHCOOCH₃ | O | 130–132 |
| 10 | Cyclopropylmethyl | O | 147–149 |
| 11 | —CH₂CH₂CN | O | 117–119 |
| 12 | —CH₂CH₂SO₂CH₃ | O | 132–133 |
| 13 | —CH₂CH₂SCH₃ | O | 112–114 |
| 14 | Cyclopentyl | O | 152–154 |
| 15 | —CH₂C(CH₃)₃ | O | 177–179 |
| 16 | —CH₂CH(CH₃)₂ | O | 137–139 |
| 17 | —CH₂CH₂OCH₃ | O | |

TABLE 2

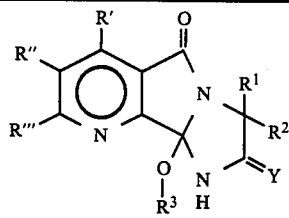

Ib

| Example | R' | R'' | R''' | R¹ | R² | R³ | Y | M.p. (°C.) |
|---|---|---|---|---|---|---|---|---|
| 18 | H | H | H | $CH_3$ | Cyclopropyl | Cyclopentyl | O | 109–117 |
| 19 | H | H | H | $CH_3$ | $CH_3$ | Cyclopentyl | O | 142–144 |
| 20 | $CH_3$ | H | H | $CH_3$ | $-CH(CH_3)_2$ | $-CH_2CH_2OC_2H_5$ | O | 141–142 |
| 21 | H | (benzo-fused) | | $CH_3$ | $-CH(CH_3)_2$ | Cyclopentyl | O | 165 |
| 22 | H | $C_2H_5O$ | H | $CH_3$ | $-CH(CH_3)_2$ | Cyclopentyl | O | |
| 23 | H | H | Cl | $CH_3$ | $-CH(CH_3)_2$ | $-CH_2CH_2OC_2H_5$ | O | |
| 24 | H | $C_2H_5$ | H | $CH_3$ | $-CH(CH_3)_2$ | Cyclopentyl | O | |
| 25 | $CH_3$ | H | H | $CH_3$ | $-CH(CH_3)_2$ | $-CH_2CH_2OCH_3$ | O | |
| 26 | $CH_3$ | H | H | $CH_3$ | $-CH(CH_3)_2$ | $-CH_2CH_2OC_6H_5$ | O | |
| 27 | H | H | H | $-(CH_2)_4-$ | | $-CH_2CH_2OC_2H_5$ | O | |
| 28 | H | H | H | $-(CH_2)_2-$ | | $-CH_2CH_2OC_2H_5$ | O | |
| 29 | H | H | H | $CH_3$ | $-CH(CH_3)_2$ | $-CH_2CH_2OC_2H_5$ | S | |
| 30 | H | $CF_3$ | H | $CH_3$ | $-CH(CH_3)_2$ | $-CH_2CH_2OC_2H_5$ | O | |
| 31 | H | $C_2H_5O$ | $NO_2$ | $CH_3$ | $-CH(CH_3)_2$ | $-CH_2CH_2OC_2H_5$ | O | 125 |
| 32 | H | $CH_3OCH_2$ | H | $CH_3$ | $-CH(CH_3)_2$ | $-CH_2CH_2OC_2H_5$ | O | |
| 33 | H | $C_2H_5O$ | $CH_3S$ | $CH_3$ | $-CH(CH_3)_2$ | $-CH_2CH_2OC_2H_5$ | O | |
| 34 | H | $C_2H_5O$ | $C_6H_5S$ | $CH_3$ | $-CH(CH_3)_2$ | $-CH_2CH_2OC_2H_5$ | O | |
| 35 | H | $C_2H_5O$ | 2-Chloro-4-trifluoro-methyl-phenoxy | $CH_3$ | $-CH(CH_3)_2$ | $-CH_2CH_2OC_2H_5$ | O | |
| 36 | H | H | H | $-C(CH_3)_2CH_2-$ | | $-CH_2CH_2OC_2H_5$ | O | |

Example 37

A solution of 2 g of 3-isopropyl-3-methyl-2H-imidazo[1',2':1,2]pyrrolo[3,4-b]pyridine-2,5(3H)-dione in 90 ml of acetone and 10 ml of water is stirred at room temperature for about 16 hours. The solution is subsequently evaporated to dryness and the residue is crystallized from ethyl acetate/n-hexane. There is obtained 1,9b-dihydro-9b-hydroxy-3-isopropyl-3-methyl-2H-imidazo[1',2':1,2]pyrrolo[3,4-b]pyridine-2,5(3H)-dione as colorless crystals, m.p. 151°–153° C.

Examples 38–40

The appropriate starting materials of formula II are treated with water in acetone analogously to the procedure described in Example 37 in order to manufacture the compounds of formula Ic listed in the following Table 3.

TABLE 3

Ic

| Example | R'' | R¹ | R² | M.p. (°C.) |
|---|---|---|---|---|
| 38 | $C_2H_5$ | $CH_3$ | $-CH(CH_3)_2$ | 146–148 |
| 39 | $C_2H_5O$ | $CH_3$ | $-CH(CH_3)_2$ | 187 |

TABLE 3-continued

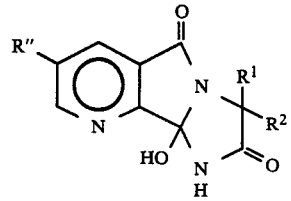

Ic

| Example | R'' | R¹ | R² | M.p. (°C.) |
|---|---|---|---|---|
| 40 | H | $-(CH_2)_4-$ | | 146–151 |

II. FORMULATION EXAMPLES

Example 41

For the preparation of an emulsifiable concentrate the ingredients listed hereinafter are mixed with one another by dissolving the active substance (possibly at an elevated temperature) in the tenside/solvent mixture:

| | |
|---|---|
| Compound of formula I (active substance) | 125 g |
| Isopropanol | 125 ml |
| Nonylphenol-(8)-ethoxylate | 50 g |
| Calcium dodecylbenzenesulphonate | 25 g |
| Acetic acid | 25 ml |
| 1,1,1-Trichloroethane | to 1000 ml |

The resulting clear concentrate emulsifies spontaneously in water. The emulsion formed is suitable as a ready-for-use spray liquor.

Example 42

For the preparation of a suspendable oil-containing concentrate the ingredients listed hereinafter are mixed with one another and the mixture is ground as finely as possible by means of a colloid or ball mill.

| | Weight percent |
|---|---|
| Compound of formula I (active substance) | 25 |
| Non-ionic/anion-active emulsifier mixture | 16 |
| Hydrated silicic acid | 1 |
| Mineral oil raffinate | 58 |

Upon stirring in water the resulting concentrate forms a homogeneous emulsion or suspension which is suitable as a ready-for-use spray liquor.

I claim:

1. A compound of the formula

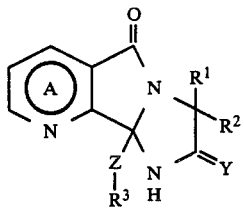

wherein
the pyridine ring A is unsubstituted or substituted with up to three substituents selected from the group consisting of halogen, $C_{1-6}$-alkyl, trifluoromethyl, $C_{1-4}$-hydroxyalkyl, $C_{1-6}$-alkoxy, $C_{1-6}$-alkylthio, nitro, cyano, methylsulphonyl, phenylsulphonyl, p-tolylsulphonyl, unsubstituted phenyl, phenoxy, phenylthio and benzyloxy and substituted phenyl, phenoxy, phenylthio and benzyloxy whereby the substituents for substituted phenyl, phenoxy, phenylthio and benzyloxy are themselves selected from the group consisting of 1 to 3 halogen atoms, 1 or 2 $C_{1-4}$-alkyl residues, a trifluoromethyl group, 1 or 2 $C_{1-4}$-alkoxy groups, 1 or 2 nitro groups and a cyano group, and
$R^1$ is unsubstituted $C_{1-4}$-alkyl or $C_{1-4}$-alkyl mono- or multiply substituted with substituents selected from the group consisting of fluorine and chlorine,
$R^2$ is $C_{1-10}$-alkyl or $C_{3-6}$-cycloalkyl, or
$R^1$ and $R^2$ together with the carbon atom to which they are attached form a $C_{3-6}$-cycloalkane ring which is unsubstituted or substituted with one or two $C_{1-4}$-alkyl residues;
$R^3$ is substituted straight or branched chain $C_{1-12}$-alkyl with the substituents selected from the group consisting of hydroxy, cyano, $C_{3-6}$-cycloalkyl, $C_{1-4}$-alkoxy, substituted or substituted phenoxy with the phenoxy substituents selected from the group consisting of 1 to 3 halogens, 1 or 2 $C_{1-4}$-alkoxy, 1 or 2 nitro, or cyano; $SO_n$, $R^4$, or $-NHCOOR^5$ wherein $R^4$ is hydroxy, methyl, phenyl or p-tolyl; n is 0-2; and $R^5$ is $C_{1-4}$ alkyl with the proviso that $n^1$ is 2 when $R^4$ is hydroxy.

2. The compound of claim 1 wherein $R^1$ is $C_{1-4}$-alkyl.

3. The compound of claim 1 wherein $R^2$ is isopropyl.

4. The compound of claim 1 wherein $R^1$ is methyl.

5. The compound of claim 1 wherein $R^3$ is selected from the group consisting of 2-methoxyethyl, 2-ethoxyethyl.

6. The compound of claim 1 wherein the compound is 1,9b-dihydro-3-isopropyl-9b-(2-methoxyethoxy)-3-methyl-2H-imidazo[1',2':1,2]pyrrolo[3,4-b]pyridine-2,5(3H)-dione.

7. The compound of claim 1 wherein the compound is 9b-(2-ethoxyethoxy)-1,9b-dihydro-3-isopropyl-3-methyl-2H-imidazo[1',2':1,2]pyrrolo[3,4-b]pyridine-2,5(3H)-dione.

8. A weed control composition comprising from 0.01 to 95 weight percent of at least one compound of the formula

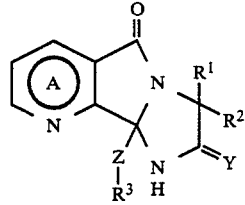

wherein
the pyridine ring A is unsubstituted or substituted with up to three substituents selected from the group consisting of halogen, $C_{1-6}$-alkyl, trifluoromethyl, $C_{1-4}$-hydroxyalkyl, $C_{1-6}$-alkoxy, $C_{1-6}$-alkylthio, nitro, cyano, methylsulphonyl, phenylsulphonyl, p-tolylsulphonyl, unsubstituted phenyl, phenoxy, phenylthio and benzyloxy and substituted phenyl, phenoxy, phenylthio and benzyloxy whereby the substituents for substituted phenyl, phenoxy, phenylthio and benzyloxy are themselves selected from the group consisting of 1 to 3 halogen atoms, 1 or 2 $C_{1-4}$-alkyl residues, a trifluoromethyl group, 1 or 2 $C_{1-4}$-alkoxy groups, 1 or 2 nitro groups and a cyano group, and
$R^1$ is unsubstituted $C_{1-4}$-alkyl or $C_{1-4}$-alkyl mono- or multiply substituted with substituents selected from the group consisting of fluorine and chlorine,
$R^2$ is $C_{1-10}$-alkyl or $C_{3-6}$-cycloalkyl, or
$R^1$ and $R^2$ together with the carbon atom to which they are attached form a $C_{3-6}$-cycloalkane ring which is unsubstituted or substituted with one or two $C_{1-4}$-alkyl residues;
$R^3$ is substituted straight or branched chain $C_{1-12}$-alkyl with the substituents selected from the group consisting of hydroxy, cyano, $C_{3-6}$-cycloalkyl, $C_{1-4}$-alkoxy, substituted or substituted phenoxy with the phenoxy substituents selected from the group consisting of 1 or more hydroxy, 1 cyano, 1 $C_{3-6}$-cycloalkyl, $C_{1-4}$-alkoxy, unsubstituted or substituted phenoxy with the phenoxy substituents selected from the group consisting of 1 to 3 halogens, 1 or 2 $C_{1-4}$ alkyl, 1 trifluromethyl, 1 or 2 $C_{1-4}$-alkoxy, 1 or 2 nitro, or 1 cyano; $SO_{n'}$, $R^4$, or $-NHCOOR^5$ wherein $R^4$ is hydroxy, methyl, phenyl or p-tolyl; $n'$ is 0-2; and $R^5$ is $C_{1-4}$ alkyl with the proviso that $n^1$ is 2 when $R^4$ is hydroxy, and Y and Z are each independently oxygen or sulphur.

9. The composition of claim 8 wherein $R^1$ is $C_{1-4}$-alkyl.

10. The composition of claim 8 wherein $R^2$ is isopropyl.

11. The composition of claim 8 wherein $R^1$ is methyl.

12. The composition of claim 8 wherein $R^3$ is selected from the group consisting of 2-methoxyethyl, 2-ethoxyethyl.

13. The composition of claim 8 wherein the compound is 1,9b-dihydro-3-isopropyl-9b-(2-methoxyethoxy)-3-methyl-2H-imidazo[1',2':1,2]pyrrolo[3,4-b]pyridine-2,5(3H)-dione.

14. The composition of claim 8 wherein the compound is 9b-(2-ethoxyethoxy)-1,9b-dihydro-3-isopropyl-3-methyl-2H-imidazo[1',2':1,2]pyrrolo[3,4-b]pyridine-2,5(3H)-dione.

* * * * *

UNITED STATES PATENT AND TRADEMARK OFFICE
CERTIFICATE OF CORRECTION

PATENT NO. : 4,741,767
DATED : May 3, 1988
INVENTOR(S) : Obrecht

It is certified that error appears in the above-identified patent and that said Letters Patent is hereby corrected as shown below:

In Claim 1, lines 53-61, please make the following changes:

"$R^3$ is substituted straight or branched chain $C_{1-12}$-alkyl with the substituents selected from the group consisting of _1 or more_ hydroxy, _1_ cyano, _1_ $C_{3-6}$-cycloalkyl, _1_ $C_{1-4}$-alkoxy, _unsubstituted_ or substituted phenoxy with the phenoxy substituents selected from the group consisting of 1 to 3 halogens, _1 or 2 $C_{1-4}$ alkyl, 1 triflouromethyl_, 1 or 2 $C_{1-4}$ alkoxy, 1 or 2 nitro, or _1_ cyano; $\underline{SO_n\text{'} R_4}$, or -NHCOOR$^5$ wherein $R^4$ is hydroxy, methyl, phenyl or p-tolyl; n is 0-2; and $R^5$ is $C_{1-4}$ alkyl with the proviso that $\underline{n}$' is 2 when $R^4$ is hydroxy,"

UNITED STATES PATENT AND TRADEMARK OFFICE
CERTIFICATE OF CORRECTION

PATENT NO. : 4,741,767
DATED : May 3, 1988
INVENTOR(S) : Obrecht

Page 2 of 3

It is certified that error appears in the above-identified patent and that said Letters Patent is hereby corrected as shown below:

In Claim 8, lines 39-52, please make the following hanges:

"$R^3$ is substituted straight or branched chain $C_{1-12}$-alkyl with the substituents selected from the group consisting of <u>1 or more</u> hydroxy, <u>1</u> cyano, <u>1</u> $C_{3-6}$-cycloalkyl, <u>1</u> $C_{1-4}$-alkoxy, <u>unsubstituted</u> or substituted phenoxy with the phenoxy substituents selected from the group consisting of 1 to 3 halogens, <u>1 or 2 $C_{1-4}$ alkyl, 1 triflouromethyl</u>, 1 or 2 $C_{1-4}$ alkoxy, 1 or 2 nitro, or <u>1</u> cyano; <u>$SO_n$' $R_4$</u>, or -NHCOOR$^5$ wherein $R^4$ is hydroxy, methyl, phenyl or p-tolyl; n is 0-2; and $R^5$ is $C_{1-4}$ alkyl with the

UNITED STATES PATENT AND TRADEMARK OFFICE
CERTIFICATE OF CORRECTION

PATENT NO. : 4,741,767
DATED : May 3, 1988
INVENTOR(S) : Obrecht

It is certified that error appears in the above-identified patent and that said Letters Patent is hereby corrected as shown below:

proviso that $\underline{n}'$ is 2 when $R^4$ is hydroxy,"

Signed and Sealed this

Thirtieth Day of August, 1988

Attest:

DONALD J. QUIGG

Attesting Officer

Commissioner of Patents and Trademarks